(12) United States Patent
Gerstenmeier (10) Patent No.: US 12,194,309 B2
(45) Date of Patent: Jan. 14, 2025

(54) PARAMETERIZED OPERATING ENVIRONMENT FOR IRRADIATION

(71) Applicant: JK-HOLDING GMBH, Windhagen (DE)

(72) Inventor: Jürgen Gerstenmeier, Neuweid (DE)

(73) Assignee: JK-HOLDING GMBH, Windhagen (DE)

( * ) Notice: Subject to any disclaimer, the term of this patent is extended or adjusted under 35 U.S.C. 154(b) by 469 days.

(21) Appl. No.: 17/600,645

(22) PCT Filed: Apr. 2, 2020

(86) PCT No.: PCT/IB2020/053147
§ 371 (c)(1),
(2) Date: Oct. 1, 2021

(87) PCT Pub. No.: WO2020/202064
PCT Pub. Date: Oct. 8, 2020

(65) Prior Publication Data
US 2022/0161048 A1 May 26, 2022

(30) Foreign Application Priority Data
Apr. 3, 2019 (CH) .................................... 00454/19

(51) Int. Cl.
*A61N 5/06* (2006.01)
*G16H 20/40* (2018.01)
*G16H 40/67* (2018.01)

(52) U.S. Cl.
CPC .......... *A61N 5/0614* (2013.01); *G16H 20/40* (2018.01); *G16H 40/67* (2018.01);
(Continued)

(58) Field of Classification Search
CPC .......... A61N 5/0614; A61N 2005/0626; A61N 2005/0661; A61N 2005/0062; G16H 20/40; G16H 40/67
See application file for complete search history.

(56) References Cited

U.S. PATENT DOCUMENTS

2005/0085877 A1   4/2005   Kratz
2010/0057651 A1   3/2010   Fung et al.
(Continued)

FOREIGN PATENT DOCUMENTS

CN    104951321 A      9/2015
DE    102013113445 A1  6/2014
(Continued)

OTHER PUBLICATIONS

German International Search Report and English Translation for International Application No. PCT/IB2020/053147, mailed Jun. 2, 2020, 16 pages.

*Primary Examiner* — Nicole M Ippolito
(74) *Attorney, Agent, or Firm* — HESLIN ROTHENBERG FARLEY & MESITI P.C.; Stephen P. Scuderi, Esq.

(57) ABSTRACT

The invention relates to an apparatus (30) for irradiating the human body or parts of the human body with optical radiation. The apparatus (30) comprises a first interface (20) for transmitting data, an analysis module (22) for creating a parameterized operating environment (23) on the basis of the transmitted data, a control unit (24) for adapting device settings on the basis of the parameterized operating environment created, and an irradiation unit (26) which receives a signal (25) from the control unit (24) according to the parameterized operating environment (23) created. The invention further relates to a system, a method and a computer program product for carrying out the method.

23 Claims, 4 Drawing Sheets

(52) U.S. Cl.
CPC ............ *A61N 2005/0626* (2013.01); *A61N 2005/0661* (2013.01); *A61N 2005/0662* (2013.01)

(56) References Cited

U.S. PATENT DOCUMENTS

| | | |
|---|---|---|
| 2013/0172963 A1 | 7/2013 | Moffat |
| 2013/0245724 A1 | 9/2013 | Kaufman |
| 2014/0052223 A1 | 2/2014 | Toepper |
| 2015/0041663 A1* | 2/2015 | Oliver .................... G01W 1/00 250/372 |
| 2015/0217130 A1 | 8/2015 | Gross et al. |
| 2015/0230863 A1* | 8/2015 | Youngquist .......... A61B 18/203 606/9 |
| 2017/0071528 A1 | 3/2017 | Chen |
| 2018/0015300 A1 | 1/2018 | Hamid |
| 2018/0243580 A1 | 8/2018 | Verhoeks et al. |
| 2018/0369604 A1 | 12/2018 | Gamelin et al. |

FOREIGN PATENT DOCUMENTS

| | | |
|---|---|---|
| EP | 1415683 A1 | 9/2003 |
| EP | 3361401 A1 | 8/2018 |
| JP | 2010264107 A | 11/2010 |
| JP | 2015503406 A | 2/2015 |
| JP | 2018163670 A | 10/2018 |
| WO | WO 2016127120 A1 | 8/2016 |
| WO | WO2018065342 A1 | 4/2018 |
| WO | WO2019020137 A1 | 1/2019 |
| WO | 2019118773 A1 | 6/2019 |

\* cited by examiner

PARAMETERIZED OPERATING ENVIRONMENT FOR IRRADIATION

This application is a national stage entry under 35 U.S.C. § 371 of International Application Number PCT/IB2020/053147, filed Apr. 2, 2020, and claims priority to Swiss application CH 00454/19, filed Apr. 3, 2019, the entire contents of which applications are hereby incorporated herein in their entireties.

The invention relates to an apparatus for irradiating the human body or parts of the human body with optical radiation. It also relates to a method, a computer program product for carrying out this method, and a system, all according to the generic terms of the independent claims.

TECHNOLOGICAL BACKGROUND

Apparatuses for irradiating the human body or parts of the human body with optical radiation are known. These are used in the medical, cosmetic and/or therapeutic fields. In the field of irradiating the skin, emitting arrangements are used, the radiation of which produces, for example, a photobiological effect in a person exposed to said radiation. The radiation hits the skin of a person but can penetrate deeper regions of the body depending on the specific wavelength. The effect comprises, for example, a tanning of the skin, but other physiological and psychological effects result from the irradiation as well. The radiation covers the spectrum of ultraviolet (UV) radiation, visible (VIS) radiation and near infrared (nIR) radiation. The UV radiation has wavelengths in the spectrum between 100 nm and approx. 380 nm, the VIS radiation has wavelengths in the spectrum between approx. 380 nm and approx. 780 nm, and the nIR radiation has wavelengths in the spectrum between approx. 780 nm and approx. 1400 nm. The mentioned spectra merge into one another. Depending on the treatment, the irradiation may be focused on a sub-spectrum of the aforementioned spectra. For this purpose, medical-cosmetic radiation-emitting arrangements can also be associated with dedicated, individual wavelengths, e.g. the UV radiation generated by five light tubes.

In the field, apparatuses for affecting the skin of a user are known, as they are used, for example, in tanning salons, in which a person to be irradiated for the purpose of tanning his/her skin by pigmentation can lie on a cover forming a lying surface or boundary surface, wherein a UV radiation-emitting arrangement, usually having multiple light tubes, in particular fluorescent tubes, is arranged below the cover. In most cases, such tanning devices also have another assembly with further light tubes and a second cover, which together can be pivoted toward the person to be irradiated, such that the person can be tanned from two sides. The problem here is that, while the user can enter any operating parameters on the apparatus, these are not matched to the user and can therefore result in disadvantages.

It is an object of the invention to specify an apparatus for irradiating the human body or parts of the human body with ultraviolet and/or optical radiation, in which a user can adjust the apparatus to his/her needs, in particular in advance or regardless of location, such that this apparatus achieves an optimized irradiation result.

DESCRIPTION OF THE INVENTION

According to the invention, this problem is solved by an apparatus with the characteristics of the independent claim.

According to one aspect of the invention, an apparatus for irradiating the human body or parts of the human body with optical radiation is designed, comprising a first interface for transferring data, an analysis module for creating a parameterized operating environment on the basis of the transmitted data, a control unit for adjusting device settings on the basis of the created parameterized operating environment, and an irradiation unit that receives a signal according to the created parameterized operating environment from the control unit.

This advantageously makes it possible to consider user-specific wishes and settings and to offer an optimal irradiation. For example, the user can generate presets for certain operating parameters in advance. It is particularly advantageous that the parameterized operating environment is determined and carried out fully automatically by the apparatus. The parameterized operating environment comprises an irradiation plan, also known as a tanning plan, which can be applied individually to a user. A user therefore has more time for the treatment or irradiation, as the parameters do not need to be set on the device at the beginning of the treatment. Device settings and, for example, an optimal tanning time can be determined by means of a stored history and imported by an application. Of course, the user has the option of making readjustments or specifying further settings.

Preferably, the first interface enables a Bluetooth connection with a user device. This makes it easy to connect the apparatus to the user device, e.g. a smartphone, tablet, or user computer, to transfer user data such as a profile or preferred presets. Depending on the user's location, i.e. if the user is in close proximity to the apparatus with a user device, the apparatus can start immediately and start reading user data and creating a parameterized operating environment. The apparatus starts fully automatically, so to speak. The user does not need to make any further adjustments on the apparatus. The first interface can also have a wired connection to a user device, such that a clear association with, and immediate connection to, the apparatus can be established. The apparatus is also referred to as an arrangement, a tanning device, or a tanner for short, and preferably has a connection, i.e. an interface, for a user device on its exterior. After connecting the user device, the user data is transmitted or imported, and the user device can be supplied with energy via the same connection, such that it charges during the use of the apparatus.

In a further embodiment, the first interface enables near-field communication (NFC). This is a transmission standard based on RFID technology for the contactless exchange of data by electromagnetic induction by means of loosely coupled coils over short distances of a few centimetres. RFID (radio-frequency identification) refers to a technology for transmitter-receiver systems for the automatic and contactless identification and localization of objects by means of electromagnetic waves.

In a further advantageous embodiment, the apparatus has a second interface, which is designed as a network interface. This second interface can be used to transfer or exchange data with a usage database. The usage database can be implemented as a relational or semi-structured database or as a database system.

The data of the usage database preferably comprise values such as usage time, frequency of use, skin type, and device settings. These values can refer to a user and be recalled accordingly. The values can also refer to multiple users, and can be used to determine values, e.g. averages or reference values, for other users or user groups. In turn, history data of other users can be used to determine optimized operating environments, and to apply the same. By analysing a user's profile, the user's skin type can be determined, which is incorporated into the parameterized operating environment and creates optimal values. For example, if the user provides a facial image or a photo of an arm or a hand, the analysis module can directly determine the skin type and consider it accordingly for an optimal operating environment.

It is particularly advantageous to store the transmitted data in the usage database in an anonymized manner. Privacy and data protection can thus be guaranteed.

The analysis module creates the parameterized operating environment on the basis of the transmitted data and/or the provided data; The analysis can be performed on a stochastic basis, but comparative analyses are also possible. The analysis results are incorporated wholly or in part in the parameterized operating environment.

If the analysis module receives data from the usage database, said data can be used as a basis for the parameterized operating environment and thus form a solid foundation for an optimal operating environment. The analysis module can preferably determine the skin type of a user, which is relevant to the parameterized operating environment. It is also possible to determine a tanning prognosis that can be given to the user. This makes it possible to perform appropriate readjustments.

In a further embodiment, the analysis module creates the parameterized operating environment on the basis of the transmitted data with regard to light-therapy treatments. The control unit then controls appropriate application routines for relaxation or biostimulation. The positive effects of biostimulating phototherapy are highly appreciated by users. Such an apparatus for biostimulating phototherapy, in particular for supplementary biostimulating phototherapy in conjunction with a therapy device, and embodiments thereof are described in the Swiss patent application by the same applicant, entitled "Apparatus for biostimulating phototherapy" with a filing date of 3 Apr. 2019, reference P100429CH and application number 00454/19.

According to a further preferred embodiment, the analysis module is arranged outside the apparatus. This way, computationally intensive tasks can be outsourced and can be carried out at any location. The results can be used and imported by any apparatus by means of the network.

Preferably, the parameterized operating environment comprises an irradiation plan. This enables the individualized irradiation of a user, e.g. with defined body regions, different intensities and wavelengths, as well as times. There are often multiple apparatuses or tanners in tanning salons. The parameterized operating environment can also be expediently used to assign appropriate apparatuses to the respective users. This makes it possible to achieve a uniform use and utilization of the apparatuses. The energy load can also be better distributed as a result.

According to a particularly preferred embodiment, the control unit performs the adjustment of the parameterized operating environment on the basis of a user's data. This allows the individual needs of a user to be addressed. The user can specify his desired irradiation, but this is then precisely matched to the user on the apparatus, such that unwanted side effects are avoided.

According to a further particularly preferred embodiment, the control unit performs the adjustment of the parameterized operating environment on the basis of the data from a usage database. The usage database stores not only values of individual users, but also reference values which are advantageous for certain skin types or user groups. If a user goes to different studios for treatment or tanning, the values from the usage database are particularly useful and can be read into each apparatus in various locations. If, for example, a user does not have his user device with him, the identification of the user can also be carried out by a voice command, e.g. an individual code linked to data from the usage database, via a microphone on the apparatus. The apparatus is equipped with a speech recognition device and voice control. Such voice control and embodiments thereof are described in the Swiss patent application by the same applicant entitled "Apparatus for affecting at least parts of a body" with a filing date of 3 Apr. 2019, reference P100446CH and application number 00454/19.

In a further design of the voice control, it is made possible by means of networking to use voice commands to, for example, have emails or messages, weather forecasts or similar online information read out during the treatment, or even to make telephone calls. The apparatus also has one or more speakers. A user can also use the microphone, i.e. the voice control, before or after a treatment. It is also possible for an operator to use voice control for communication, maintenance work, instructions, information retrieval or the like.

One aspect of the present invention relates to a method for operating an apparatus for irradiating the human body or parts of the human body with optical radiation.

Another aspect of the present invention relates to a computer program product for carrying out a method according to the invention on a computer for controlling an apparatus for irradiating the human body or parts of the human body with optical radiation.

Yet another aspect of the present invention relates to a system or components for creating a parameterized operating environment for irradiating the human body or parts of the human body with optical radiation. The system comprises an interface for transmitting a user's first data, a usage database that receives, stores or provides second data, an analysis module for creating a parameterized operating environment on the basis of said transmitted first data and said provided second data, a control unit for adjusting device settings on the basis of the created parameterized operating environment, and an irradiation unit which receives a signal according to the created parameterized operating environment from the control unit.

The usage database can be provided locally in a tanning salon, or salon for short. Preferably, the usage database is implemented as a cloud service. This enables easy storage, maintenance, and backup of data and allows time-independent access by users.

According to a particularly preferred embodiment, multiple apparatuses are connected to, or coupled with, the usage database via a connection. As a result, data from a wide variety of devices and users can be merged, which results in optimized operating environments through evaluation and analysis.

Expediently, the analysis module outputs user-specific recommendations for the parameterized operating environment with an irradiation plan. These recommendations can be stored in the usage database and recalled by a user. Alternatively, the recommendations are transferred to a user device, can be edited there, and stored in the profile or the usage database.

Preferably, a user device accesses the usage database via an Internet connection. For data security reasons, an encrypted connection, e.g. via https, is preferable. If the usage database is local, e.g. located in a salon, a user device can also access it locally.

According to an embodiment, the user device receives usage database data from the usage database, which can be individualized by the user accordingly. These data can then be used to create a parameterized operating environment. The user can also provide feedback via the user device, which will then be taken into account in the future or incorporated into further analyses.

Once a user has created and saved a profile, e.g. containing the desired duration, intensity, temperature, music, etc., the stored profile can be transmitted to an apparatus to create the optimal operating environment and device settings. For an optimal tanning time, a stored history can also be used. In a preferred embodiment, the desired data as well as the operating environment and device settings are stored in the usage database. The determination of an optimal operating environment allows intelligent tanning, also referred to as smart tanning.

A user's profile can preferably be stored in an application, e.g. in an app, on a user's smartphone. Sensitive user data is then not stored in the apparatus or in the salon, which would require complex security measures, but on the user's device.

Recording the procedure and/or measuring an exposure duration and displaying a maximum increases user safety. The values can be stored in the usage database and/or in the user device and made available for future treatments. The display can be made on the apparatus or via said application.

For a person skilled in the art, it is self-evident that all embodiments described here can be realized in a design according to the present invention, unless they are explicitly mutually exclusive.

In the following, the present invention is explained in more detail on the basis of concrete embodiments and drawings, but without being limited to the same.

After studying these particular embodiments and drawings, further advantageous embodiments of the present invention may become apparent to a person skilled in the art.

DESCRIPTION OF THE DRAWINGS

Embodiments of the invention are described on the basis of the following drawings, wherein identical reference signs denote identical or similar parts.

CARRYING OUT THE INVENTION

Figure 1:
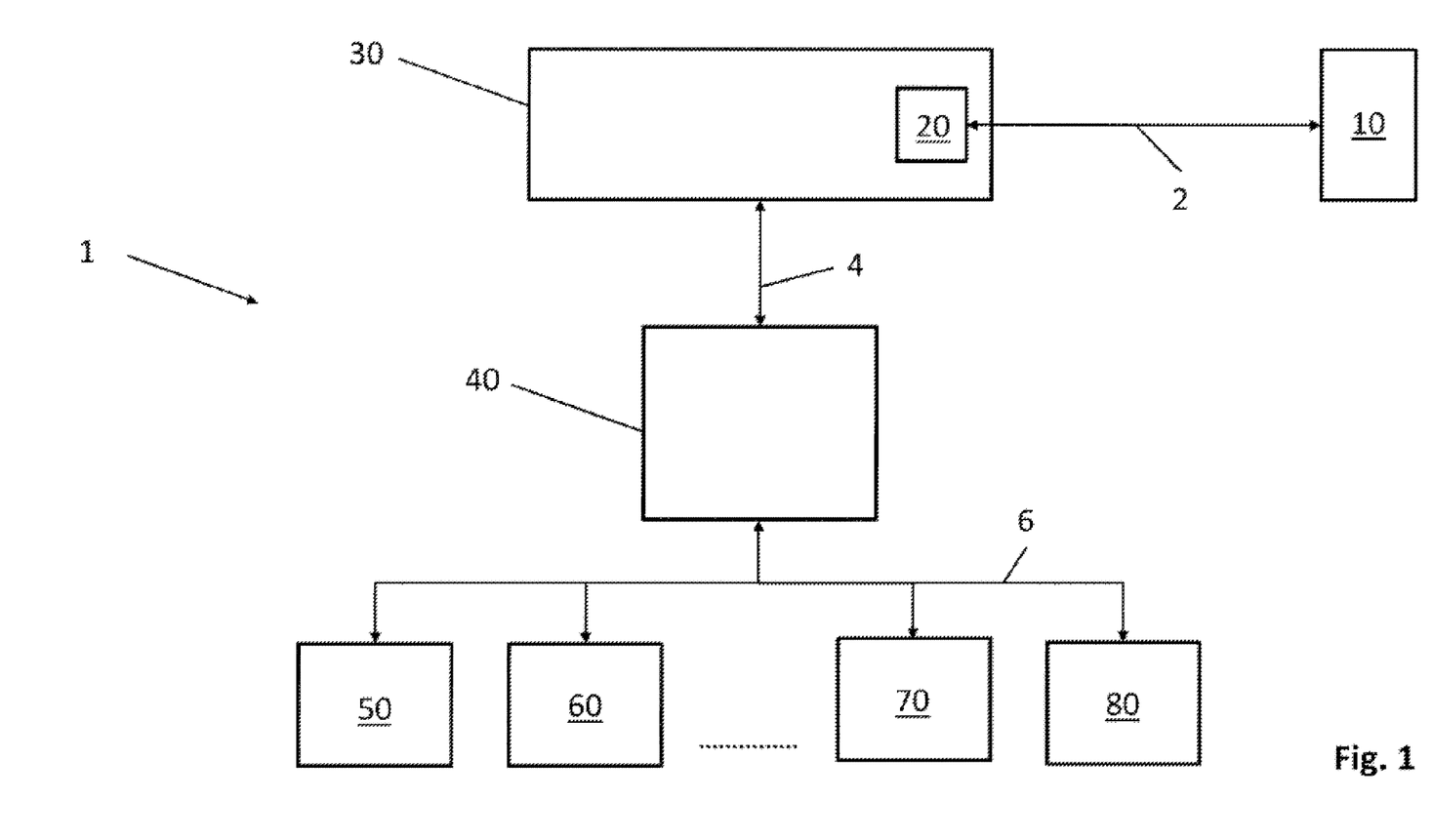
FIG. 1 schematically shows an arrangement having multiple apparatuses, a usage database, and a user device.

FIG. 1 shows a system 1 with multiple components. The apparatus 30 is designed for irradiating the human body or parts of the human body with optical radiation. The apparatus 30 is equipped with an interface 20, via which a first connection 2 with a user device 10 can be established. The user device 10, which may be a smartphone, tablet, or another application-executing device, is connected via the first, wired connection 2 to the apparatus 30 via the interface 20 and can exchange data via said connection 2. The apparatus 30 is connected to a usage database 40 via a second connection 4. The usage database 40 is connected to further apparatuses 50, 60, 70, 80 via a third connection 6.

Further apparatuses can be connected to the usage database 40. Each apparatus 30, 50, 60, 70, 80 can be the same or a different irradiation or tanning apparatus. The data transmission via the second connection 4 and the third connection 6 is preferably carried out via LAN or WLAN.

Figure 2:
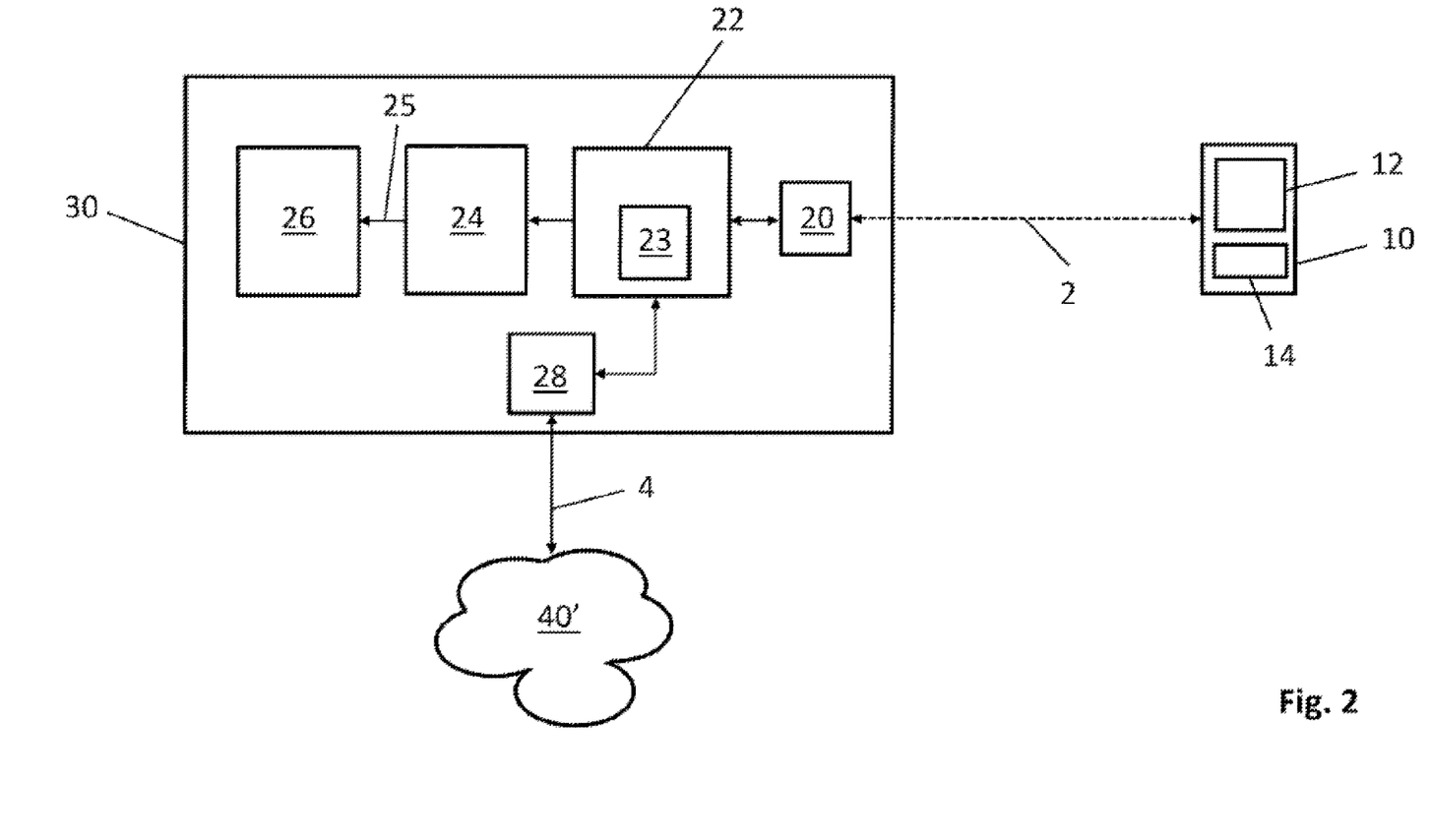
FIG. 2 schematically shows an arrangement of an apparatus according to the invention, coupled with a usage database and a user device.

FIG. 2 shows an apparatus 30 which is wirelessly connected to the user device 10, e.g. via Bluetooth®, WLAN (Wireless Local Area Network), or near-field communication. The user device 10 has a display 12 for displaying information and an input unit 14. Display 12 and input unit 14 can be merged and combined into one unit. A user records his profile or desired settings on the display 12, which are then transmitted to the interface 20, hereinafter also called first interface 20.

The apparatus 30 further comprises an analysis module 22 for creating a parameterized operating environment 23, a control unit 24, and an irradiation unit 26. The analysis module 22 comprises a computing unit for processing data. The apparatus 30 is equipped with a second interface 28, which is connected to the analysis module 22. The second interface 28 is connected to the usage database 40'-which is executed as a cloud service in the example shown here—via a second connection 4. The analysis module 22 is connected to the control unit 24. The control unit 24 adjusts the device settings on the basis of the created parameterized operating environment. The control unit 24 sends a signal 25 to the irradiation unit 26 according to the created parameterized operating environment. The parameterized operating environment is determined by the analysis module 22 on the basis of the data transmitted from the user device 10 and/or the usage database 40'. The control unit 24 then adjusts or sets the device settings. A wide variety of values are incorporated into determining the optimal operating environment. On the one hand, specifications, such as those stored in a profile, are given by the user, and on the other hand, values from the usage database 40' are used to determine the optimal operating environment. In general, the parameterized operating environment contributes to the comfort of a user, as values such as preferred intensity, temperature, but also optimal exposure duration can be set. In the case of multiple tanning apparatuses, the parameterized operating environment enables an improved control of the utilization and use of individual apparatuses.

The control unit 24 controls the irradiation unit 26, which, for example, emits actinic radiation, via a signal 25 according to the created parameterized operating environment 23. This has the advantage that certain body regions can be treated with defined intensity and duration in order to achieve an optimal result.

Figure 3:
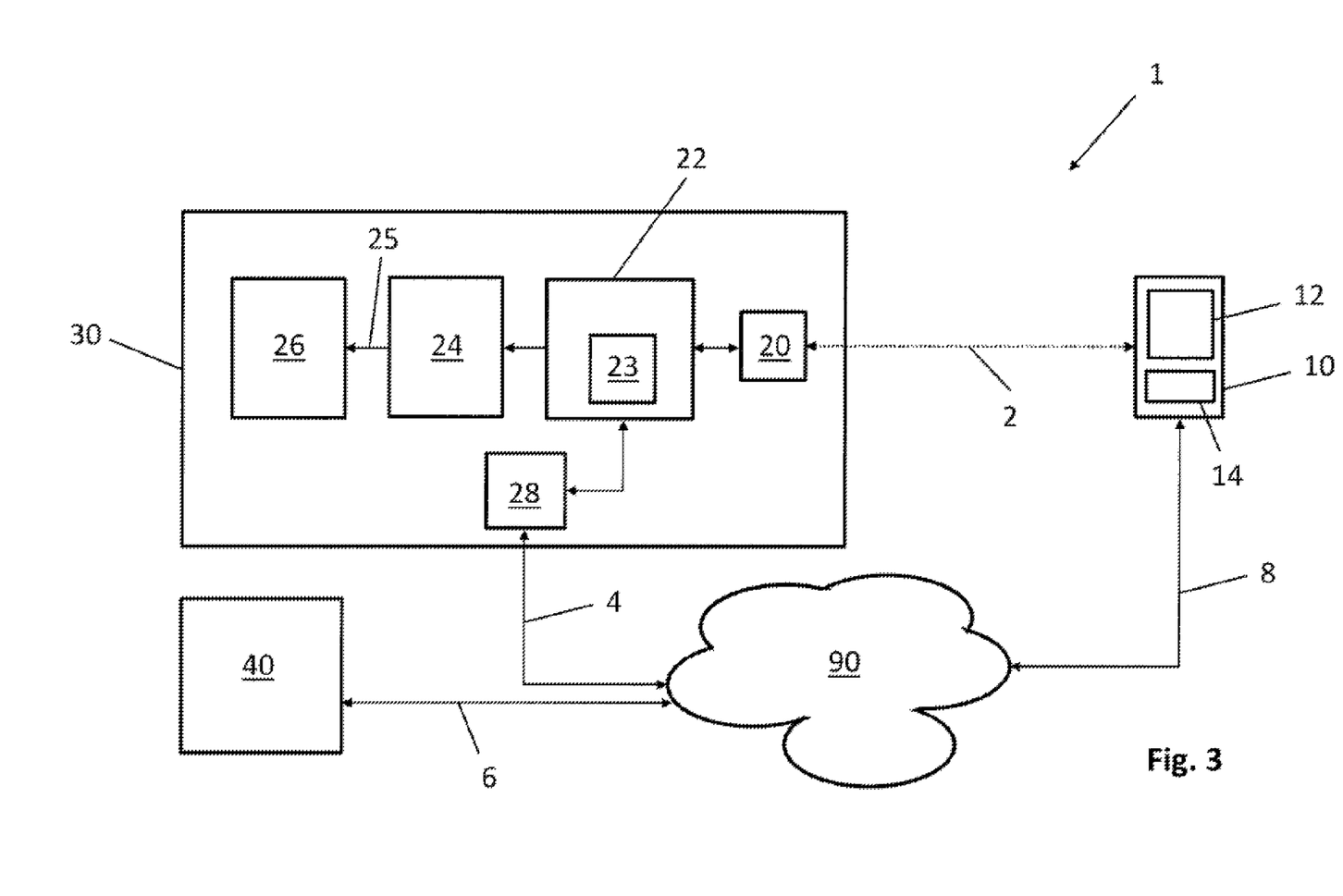
FIG. 3 schematically shows an arrangement of an apparatus according to the invention, coupled with a usage database, and a connection between a user device and said usage database.

FIG. 3 shows the system 1 in a further preferred embodiment. The apparatus 30 is designed for irradiating the human body with medical-cosmetic radiation. Herein, the first interface 20 is connected to the user device 10 via the first connection 2 by means of WLAN (Wireless Local Area Network). Particularly preferably, the interface 20 comprises a module with a microchip with a 2.4 GHz 802.11b/g/n WLAN capacity. Other wireless connection types are entirely possible, as are wired connections. The user device 10 transmits data stored in the user device 10. The apparatus 30 receives this data via the first interface 20 and forwards it to the analysis module 22 for further processing.

The apparatus 30 is connected to a network 90, such as the Internet, via the second connection 4. The network 90 can run as a LAN (Local Area Network), WAN (wide-area network), WLAN (Wireless Local Area Network), or proprietary network. The user device 10 is connected to the network 90 via a fourth connection 8. The usage database 40 is connected to the network 90 via a third connection 6. This allows the data of a user from the user device 10 to be stored directly in the usage database 40. The user can also receive information from the usage database 40. Such information can include evaluations, preferred free appointments or periods, but also advertising. This is particularly effective if the usage database 40 acts as a cloud service, as described in FIG. 2. The usage database 40' is then not a pure database but can be provided with modules for analysing the data, which generate added value.

Figure 4:
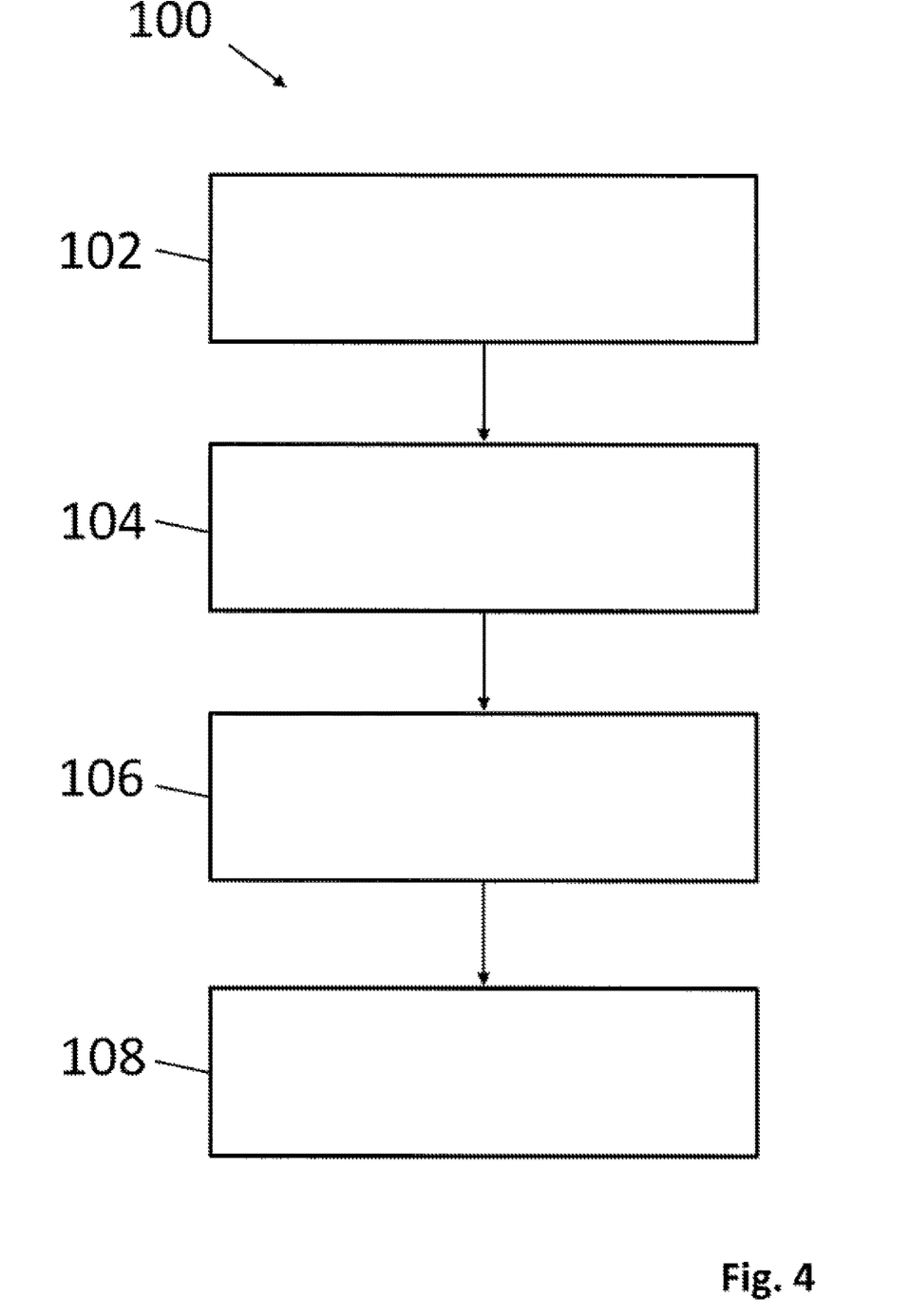
FIG. 4 shows a schematic sequence of steps.

FIG. 4 shows a schematic step sequence 100 for operating an apparatus 30 for irradiating the human body or parts of the human body with optical radiation.

In step 102, data of a user are transmitted via the interface 20. Herein, the interface 20 can be designed for sending and receiving, i.e. it can be bidirectional. In a further embodiment, the interface 20 is provided only for receiving data. This unidirectional connection only allows data to be imported to the apparatus 30. An optimal operating environment can be created in combination with other data, such as data from the previously described usage database 40, 40'.

In step 104, a parameterized operating environment 23 is created on the basis of the transmitted or received data. Because the transmitted or received data contain user-specific values and information, they can be analysed and matched or correlated with the usage database 40, 40' to provide an optimal operating environment 23 for the user. This process is performed by the analysis module 22, which is preferably located in the apparatus 30.

In step 106, device settings are adjusted on the basis of the created parameterized operating environment 23. Thus, individual wishes and preferences of a user, but also system- and apparatus-relevant conditions, can be taken into account. The control unit 24 performs the adjustments.

In step 108, the device settings for irradiation are applied. In one embodiment, the irradiation unit 26 receives a signal 25 according to the created parameterized operating environment 23 from the control unit (24). This enables optimal irradiation according to the created parameterized operating environment 23.

With the present invention, an apparatus, a system, a method, and a computer program product for operating the method was provided, which remedies at least one disadvantage of the known prior art.

The invention claimed is:

1. An apparatus for irradiating the human body or parts of the human body with optical radiation, comprising:
 a. a first interface for transmitting data;
 b. an analysis module for creating a parameterized operating environment on the basis of said transmitted data;
 c. a control unit for adjusting device settings on the basis of the created parameterized operating environment; and
 d an irradiation unit which receives a signal of the created parameterized operating environment from the control unit,
  wherein the transmitted data is used to create a user profile, and the user profile is stored on a user device.

2. The apparatus of claim 1, wherein the first interface enables a Bluetooth connection with the user device.

3. The apparatus of claim 1, wherein the first interface has a wired connection with a user device.

4. The apparatus of claim 1, further comprising a second interface, in particular a network interface, for transmitting data to/from a usage database.

5. The apparatus of claim 4, wherein the analysis module receives data of the usage database and uses said data as the basis for the parameterized operating environment.

6. The apparatus of claim 1, wherein the analysis module is arranged outside the apparatus.

7. The apparatus of claim 1, wherein the parameterized operating environment comprises an irradiation plan.

8. The apparatus of claim 1, wherein the control unit performs the adjustment of the parameterized operating environment on the basis of a user's data.

9. The apparatus of claim 1, wherein the control unit performs the adjustment of the parameterized operating environment on the basis of data of a usage database.

10. A method for operating an apparatus of claim 1 for irradiating the human body or parts of the human body with optical radiation, comprising the steps of:
 a. transmitting a user's data via an interface;
 b. creating a parameterized operating environment on the basis of said transmitted data;
 c. adjusting device settings on the basis of the created parameterized operating environment; and
 d. applying the device settings for irradiation according to the created parameterized operating environment.

11. The method of claim 10, wherein the transmitted data comprise one or more of the following pieces of information: presets, a profile, a partial profile, a history of previous irradiations.

12. The method of claim 10, further comprising transmitting data from a usage database, wherein the data preferably comprise one or more of the following values: usage time, frequency of use, skin type, and device settings.

13. The method of claim 12, wherein the transmission of data from the usage database comprises historical data of other users.

14. The method of claim 10, wherein the creation of the parameterized operating environment comprises an analysis of the profile of the user, whereby the skin type of the user is determined.

15. A computer program product for carrying out the method of claim 10.

16. A system for creating a parameterized operating environment for irradiation of the human body or parts of the human body with optical radiation, comprising:
 a. an interface for transmitting a user's first data;
 b. a usage database providing second data;
 c. an analysis module for creating a parameterized operating environment on the basis of said transmitted first data and said provided second data;
 d. a control unit for adjusting device settings on the basis of the created parameterized operating environment; and
 e an irradiation unit which receives a signal according to the created parameterized operating environment from the control unit,
  wherein the transmitted data is used to create a user profile, and the user profile is stored on a user device.

17. The system of claim 16, wherein the usage database contains second data having one or more of the following values: duration of use, frequency of use, skin type, and device settings.

18. The system of claim 16, wherein the transmitted first data are stored in the usage database in an anonymized manner.

19. The system of claim 16, wherein the usage database is implemented as a cloud service.

20. The system of claim 16, wherein multiple apparatuses are connected to the usage database via a connection.

21. The system of claim 16 wherein the analysis module outputs user-specific recommendations for the parameterized operating environment with an irradiation plan.

22. The system of claim 16, wherein a user device accesses the usage database via a network connection.

23. The system of claim 22, wherein the user device receives usage database data from the usage database, which, following the individualization of said data, results in the creation of the parameterized operating environment in one or more apparatuses.

* * * * *